United States Patent [19]
Lyle et al.

[11] Patent Number: 5,605,671
[45] Date of Patent: Feb. 25, 1997

[54] RADIOLABELED NEUTROPHIL ACTIVATING PEPTIDES FOR IMAGING

[75] Inventors: Leon R. Lyle, Webster Groves, Mo.; Steven L. Kunkel; Robert M. Strieter, both of Ann Arbor, Mich.

[73] Assignees: The Regents of The University of Michigan, Ann Arbor, Mich.; Mallinckrodt Medical, Inc., St. Louis, Mo.

[21] Appl. No.: 235,659

[22] Filed: Apr. 29, 1994

Related U.S. Application Data

[63] Continuation-in-part of Ser. No. 956,862, Oct. 5, 1992, Pat. No. 5,413,778, and Ser. No. 956,863, Oct. 5, 1992, Pat. No. 5,346,686.

[51] Int. Cl.⁶ .................... A61K 49/02; A61K 51/08; C07K 1/00
[52] U.S. Cl. .................... 424/1.41; 530/402; 530/408; 530/409; 530/351
[58] Field of Search .................. 424/1.41, 1.69, 424/1.49, 1.11; 530/402, 408, 409, 351, 300, 324, 357; 930/141

[56] References Cited

U.S. PATENT DOCUMENTS

| | | |
|---|---|---|
| 4,276,280 | 6/1981 | Akerkar et al. . |
| 4,520,112 | 5/1985 | Snyder et al. . |
| 4,656,280 | 4/1987 | Garlick . |
| 4,659,839 | 4/1987 | Nicolotti et al. . |
| 4,732,974 | 3/1988 | Nicolotti et al. . |
| 4,832,940 | 5/1989 | Ege . |
| 4,837,003 | 6/1989 | Nicolotti . |
| 4,926,869 | 5/1990 | Rubin et al. . |
| 4,965,392 | 10/1990 | Fritzberg et al. . |
| 4,986,979 | 1/1991 | Morgan, Jr. et al. . |
| 5,037,630 | 8/1991 | Fritzberg et al. . |
| 5,079,228 | 1/1992 | Cohen et al. . |
| 5,120,525 | 6/1992 | Goldenberg . |
| 5,179,078 | 1/1993 | Rollins et al. . |
| 5,196,510 | 3/1993 | Rodwell et al. . |
| 5,198,424 | 3/1993 | McEver . |
| 5,225,180 | 7/1993 | Dean et al. . |
| 5,241,049 | 8/1993 | Goodman et al. . |

FOREIGN PATENT DOCUMENTS

| | | |
|---|---|---|
| 0284071 | 9/1988 | European Pat. Off. . |
| 0398143 | 11/1990 | European Pat. Off. . |
| 9002762 | 3/1990 | WIPO . |
| 9013317 | 11/1990 | WIPO . |
| 9116919 | 11/1991 | WIPO . |
| 9204372 | 3/1992 | WIPO . |

OTHER PUBLICATIONS

Moser et al., "Neutrophil–activating Peptide 2 . . . or Human Neutrophils*", The Jour. of Biological Chemistry, vol. 266, No. 16, pp. 10666–10671, 1991.

Walz et al., "Generation of the Neutrophil–Activating Peptide NAP–2 From Platlet Basic Protein or Connective Tissue–Activating Peptide III through Monocyte Proteases", J. Exp. Med., vol. 171, pp. 449–454; 1990, Feb.

J. Wang et al., "Human Recombinant Macrophage Inflammatory Protein–1α and –β and Monocyte . . . ", J. Immunol., vol. 150, No. 7, pp. 3022–3029, (Apr. 1, 1993).

A. K. Samanta et al., "Interleukin 8 (Monocyte–derived Neutrophil Chemotactic Factor) . . . ", J. Biol. & Chem., vol. 285, No. 1, pp. 183–189, (Jan. 6, 1990).

Schnitzel, W., et al., "Neutorphil Activating Peptide–2 Binds with Two Affinities to . . . ", Biochem. & Biophys. Res. Comm., vol. 1, No. 1, pp. 301–307, (Oct. 15, 1991).

(List continued on next page.)

Primary Examiner—Gary E. Hollinden
Assistant Examiner—Michael G. Hartley
Attorney, Agent, or Firm—Rothwell, Figg, Ernst & Kurz

[57] ABSTRACT

A method of imaging a target site in an animal's body in which a labelled chemokine is introduced into the animal's body and allowed to accumulate at a target site which includes corresponding receptor molecules. The accumulated, labelled chemokine material then is detected so as to image the target site of the body.

25 Claims, 1 Drawing Sheet

OTHER PUBLICATIONS

Horuk, R., et al., "Purification, Receptor Binding Analysis . . . ", Journ. Biolog. Chem., vol. 268, No. 1, pp. 541–546, (Jan. 5, 1993).

Neote, K., et al., "Identification of a Promiscuous Inflammatory . . . ", Journ. Biolog. Chem., vol. 268, No. 17, pp. 12247–12249, (Jun. 15, 1993).

Besemer, J., et al., "Specific Binding, Internalization, and Degredation of Human . . . ", Journ. Biolog. Chem., vol. 264, No. 29, pp. 17409–17415, (Oct. 15, 1989).

Elner, V. M., et al., "Rapid Communication . . . ", Amer. Journ. Pathol., vol. 136, No. 4, pp. 745–750, (Apr. 1990).

Standiford, T. J., et al., "Disparate Regulation of Interleukin 8 Gene Expression From Blood . . . ", Biochem. & Biophys. Res. Comm., vol. 171, No. 2, pp. 531–536, (Sep. 14, 1990).

Thornton, A. J., et al., "Cytokine–Induced Gene Expression . . . ", J. Immuno., vol. 144, No. 7, pp. 2609–2613, (Apr. 1, 1990).

Samanta, A. K., et al., "Identification and Characterization of Specific Receptors for . . . ", J. Exper. Med., vol. 169, pp. 1185–1189, (Mar. 1989).

Hebert, C. A., et al., "Endothelial and Leukocyte Forms of IL–8 . . . ", J. Immuno., vol. 145, No. 9, pp. 3033–3040, (Nov. 1, 1990).

Darbonne, W. C., et al., "Red Blood Cells Are a Sink for Interleukin 8, a Leukocyte Chemotaxin", J. Clin. Invest., vol. 88, pp. 1362–1369, (Oct. 1991).

Ross, R., "Medical Progress: The Pathogenesis of Atherosclerosis . . . ", New Eng. J. of Med., vol. 314, No. 8, pp. 488–500. (Feb. 20, 1986).

Grob, P. M., et al., "Characterization of a Receptor for Human Monocyte–derived . . . ", J. Biolog. Chem., vol. 265, No. 14, pp. 8311–8316, (May 15, 1990).

Clark–Lewis, I., et al., "Platelet factor 4 binds to interleukin 8 . . . ", Proc. Natl. Acad. Sci., vol. 90, pp. 3574–3577, (Apr. 1993).

Rot, Antal, "Binding of Neutrophil Attractant/Activation Protein–1 . . . ", Chemical Abstracts, vol. 119, No. 21, (Nov. 22, 1993) and Cytokine, vol. 4, No. 5, pp. 347–352, (1992). Abstract.

Vita, N., et al., "Functional Linkage of the Gro.Beta and IL–8 Receptors on the Surface . . . ", Chemical Abstracts, vol. 120, No. 9, and Eur. Cytokine Network, vol. 4, No. 3, pp. 197–204, (1993). Abstract.

FIG. 1

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
        ( A ) LENGTH: 76 amino acids
        ( B ) TYPE: amino acid
        ( C ) STRANDEDNESS: Not Relevant
        ( D ) TOPOLOGY: linear     ( i i ) MOLECULE TYPE: peptide     ( v ) FRAGMENT TYPE: N-terminal     ( x i ) SEQUENCE DESCRIPTION: SEQ ID NO:1:

```
Xaa Pro Asp Ala Ile Asn Ala Pro Val Thr Cys Cys Tyr Asn Phe Thr
 1               5                  10                  15

Asn Arg Lys Ile Ser Val Gln Arg Leu Ala Ser Tyr Arg Arg Ile Thr
            20                  25                  30

Ser Ser Lys Cys Pro Lys Glu Ala Val Ile Phe Lys Thr Ile Val Ala
        35              40                  45
```

```
Lys  Glu  Ile  Cys  Ala  Asp  Pro  Lys  Gln  Lys  Trp  Val  Gln  Asp  Ser  Met
     50                      55                      60

Asp  His  Leu  Asp  Lys  Gln  Thr  Gln  Thr  Pro  Lys  Thr
65                  70                      75
```

( 2 ) INFORMATION FOR SEQ ID NO:2:

( i ) SEQUENCE CHARACTERISTICS:
        ( A ) LENGTH: 72 amino acids
        ( B ) TYPE: amino acid
        ( C ) STRANDEDNESS: Not Relevant
        ( D ) TOPOLOGY: Not Relevant     ( i i ) MOLECULE TYPE: peptide     ( v ) FRAGMENT TYPE: N-terminal     ( x i ) SEQUENCE DESCRIPTION: SEQ ID NO:2:

```
Ser  Ala  Lys  Glu  Leu  Arg  Cys  Gln  Cys  Ile  Lys  Thr  Tyr  Ser  Lys  Pro
1                   5                        10                      15

Phe  His  Pro  Lys  Phe  Ile  Lys  Glu  Leu  Arg  Val  Ile  Glu  Ser  Gly  Pro
               20                       25                      30

His  Cys  Ala  Asn  Thr  Glu  Ile  Ile  Val  Lys  Leu  Ser  Asp  Gly  Arg  Glu
          35                      40                      45

Leu  Cys  Leu  Asp  Pro  Lys  Glu  Asn  Trp  Tyr  Gln  Arg  Val  Val  Glu  Lys
     50                  55                      60

Phe  Leu  Lys  Arg  Ala  Glu  His  Ser
65                  70
```

RADIOLABELED NEUTROPHIL ACTIVATING PEPTIDES FOR IMAGING

CROSS-REFERENCES TO RELATED APPLICATIONS

This application is a continuation-in-part of U.S. patent application Ser. Nos. 07/956,862 and 07/956,863, both filed Oct. 5, 1992, which issued into U.S. Pat. Nos. 5,413,778 and 5,346,686, respectively.

BACKGROUND OF THE INVENTION

1. Field of the Invention

The present invention relates to the field of labelled peptides, peptides carrying radioactive agents, and medical uses thereof.

2. Description of the Background Art

Labelled peptides and peptides carrying radioactive agents have various therapeutic and diagnostic medical uses. Peptides carrying radioactive agents are known to be therapeutically useful in the treatment of tumors.

An important diagnostic use of labelled peptides is as imaging agents. For example, U.S. Pat. No. 4,926,869 to Rubin et al. discloses detection of an inflammation site in an individual by administering to the individual a labelled immunoglobulin or fragment thereof. The labelled immunoglobulin accumulates at the site of inflammation, thereby permitting radiographic imaging of the site utilizing known imaging techniques.

Other publications which describe the imaging of sites of infection or inflammation, utilizing labelled peptides and peptides carrying radioactive agents, include International Patent Publication Nos. WO 90/10463 and WO 90/13317.

There remains a need in the art for labelled peptides and peptides carrying radioactive agents which can be utilized for medical purposes.

SUMMARY OF THE INVENTION

In accordance with the present invention, a labelled chemokine selected from the group consisting of labelled CC chemokines and labelled CXC chemokines is utilized to image a target site in an animal's body. The labelled chemokine is introduced into the animal's body, and allowed to accumulate at the target site, which has complementary receptor molecules. The accumulated, labelled chemokine then is detected so as to image the target site.

DETAILED DESCRIPTION OF THE PREFERRED EMBODIMENTS

The present invention involves utilization of labelled chemotactic/attractant cytokines (or chemokines) selected from the group consisting of labelled CC chemokines and labelled CXC chemokines, as defined below, wherein C represents a conserved cysteine and X represents a variable amino acid.

One embodiment of the present invention utilizes a Monocyte Chemoattractant Protein (MCP)material, such as Monocyte Chemoattractant Protein-1 (MCP-1), a member of the CC family of chemokines, an analog, homolog, derivative or fragment thereof, or a peptide having specificity for a receptor of a CC chemokine such as MCP-1 (hereinafter sometimes referred to collectively as CC chemokines, CC chemokine material, Monocyte Chemoattractant Protein material or MCP material). In addition to MCP-1, other CC chemokines as referred to herein include: MIP-1$_\alpha$, MIP-1$_\beta$, RANTES, C-10, I-309, MCP-2 (also known as HC14), MCP-3 and at least one other CC chemokine which has not yet been completely characterized, as well as peptides having specificity for receptors thereof.

Labelled CC chemokine material in accordance with the present invention can be utilized to image sites of infection, inflammation, neoplasm, restenosis and atheromatous lesions in the body. Such sites include complementary receptor molecules, such as MCP receptor molecules having areas which are complementary to corresponding MCP material.

Restenosis and the development of atheromatous lesions share the common pathological element of proliferation of vascular smooth muscle. Growth factors which induce this proliferation arise in part, from monocytes which infiltrate the area in response to inflammatory stimuli. MCP-1 is a chemokine which is produced by injured vascular smooth muscle and is a potent stimulator of monocyte chemotaxis with very high specificity for monocytes and macrophage cells, which have complementary MCP receptor molecules.

In preferred embodiments, the CC chemokine material utilized in accordance with the present invention is human MCP-1, or an analog, homolog, fragment or derivative thereof having specificity for receptors of MCP-1.

Mature human MCP-1 is about 76 amino acid residues in length with a molecular weight of approximately 12.5 kD. The amino acid sequence of MCP-1 (SEQ ID No: 1) is shown below:

NH$_2$ X P D A I N A P V T C C Y N F T N R K I S V Q R L

A S Y R R I T S S K C P K E A V I F K T I V A K E I C

A D P K Q K W V Q D S M D H L D K Q T Q T P K T COOH, wherein the letters between the NH$_2$ group and the COOH group represent amino acids as follows: A represents Alanine, R represents Arginine, N represents Asparagine, D represents Aspartic acid, C represents Cysteine, Q represents Glutamine, E represents Glutamic acid, G represents Glycine, H represents Histidine, I represents Isoleucine, L represents Leucine, K represents Lysine, F represents Phenylalanine, P represents Proline, S represents Serine, T represents Threonine, W represents Tryptophan, X represents a variable amino acid, Y represents Tyrosine and V represents Valine, or a suitable derivative thereof.

The present invention is further applicable to derivatives of CC chemokine material in which retroinverse or other non-hydrolyzable linkages have been inserted, or D-amino acids substitutions have been made or peptidomimetic organic molecules have been utilized, in order to modify the native sequence.

In preferred embodiments, the CC chemokine material carries a label or radioactive agent such as indium, iodine, technetium, rhenium, gallium, samarium, holmium, yttrium, copper, cobalt and the like. In particularly preferred embodiments, the CC chemokine material carries a radioactive label selected from the group consisting of technetium-99m, indium-111, copper-62, iodine-123, iodine-131, rhenium-186 and rhenium-188.

In another embodiment, the labelling agent for the CC chemokine material is a stable isotope such as carbon-13, so as to permit detection of sites of infection, inflammation, neoplasm, atheromatous lesion or restenosis by magnetic resonance spectroscopy.

The present invention is also applicable to Interleukin-8 (IL-8) material, a member of the CXC family of chemotactic/chemoattractant cytokines (or chemokines), an analog, homolog, derivative or fragment thereof, or a peptide having specificity for a receptor of a CXC chemokine such as Interleukin-8 (hereinafter sometimes referred to collectively as CXC chemokines, CXC chemokine materials, Interleukin-8 material or IL-8 material).

The CXC family of chemotactic cytokines includes, but is not limited to, Interleukin-8, Macrophage Inflammatory Protein-2 (MIP-2), Growth Regulated Gene Products (GRO) including $GRO_\alpha$, $GRO_\beta$, and $GRO_\gamma$, Melanoma Growth Simulating Activity (MGSA), Platelet Factor-4 (PF-4), Gamma-interferon Inducible Protein (gamma-IP), Platelet Basic Protein, Connective Tissue Activating Protein (CTAP-III), Beta-thromoboglobulin (β-TG), Neutrophil-activating Peptide-2 (NAP-2), Chicken v-src-inducible Protein, Epithelial Cell-Derived Neutrophil-Activating Factor-78(ENA-78), Monokine Induced by Gamma Interferon (MIG) and peptides having specificity for receptors thereof.

In preferred embodiments, the CXC chemokine utilized is human Interleukin-8, NAP-2, or an analog, homolog, fragment or derivative thereof, having specificity for receptors of IL-8.

Examples of peptide fragments having specificity for receptors of IL-8 are described in U.S. Pat. No. 5,079,228, incorporated herein by reference.

Mature human IL-8 is approximately 72 amino acid residues in length with a molecular weight of approximately 8 kD, although there are a 77 residue and a few other variant forms.

The chemokine interleukin-8 (IL-8), also known as neutrophil-activating protein-1 (NAP-1), neutrophil-activating factor (NAF), or neutrophil chemotactic factor (NCF), is produced by many cell types in response to a variety of inflammatory stimuli, including lipopolysaccharide, interleukin-1, and tumor necrosis factor. It directly mediates neutrophil recruitment, accumulation, and activation. Its effects in vitro resemble those of other neutrophil chemoattractants (C5a, bacterial chemotaxins, leukotrienes, and platelet activating factor). Yet in contrast to these, IL-8 exhibits high specificity for neutrophils; it is stable, and its effects are long-acting but not species-specific in biological systems. IL-8 may represent a common pathway by which other chemotaxins exert their effects in vivo. As noted above, the major form of IL-8 is a polypeptide of 72 amino acid residues, with $M_r$~8 kDa on SDS-polyacrylamide gel electrophoresis. IL-8 binds with picomolar to nanomolar affinities to abundant receptors (20,–80,000 per cell) on the plasma membrane of neutrophils, and activates these cells via a GTP-binding protein in a process requiring calcium and protein kinase C. Following binding and activation, IL-8 is internalized and rapidly degraded by the neutrophils.

Members of the CXC family of cytokines (CXC chemokines) generally are basic heparin binding polypeptides having proinflammatory and reparative activities. Typical members of the group are 8–10 kD cytokines, and those members other than Interleukin-8 generally having at least about 20–45% homology with Interleukin-8.

Figure 1:
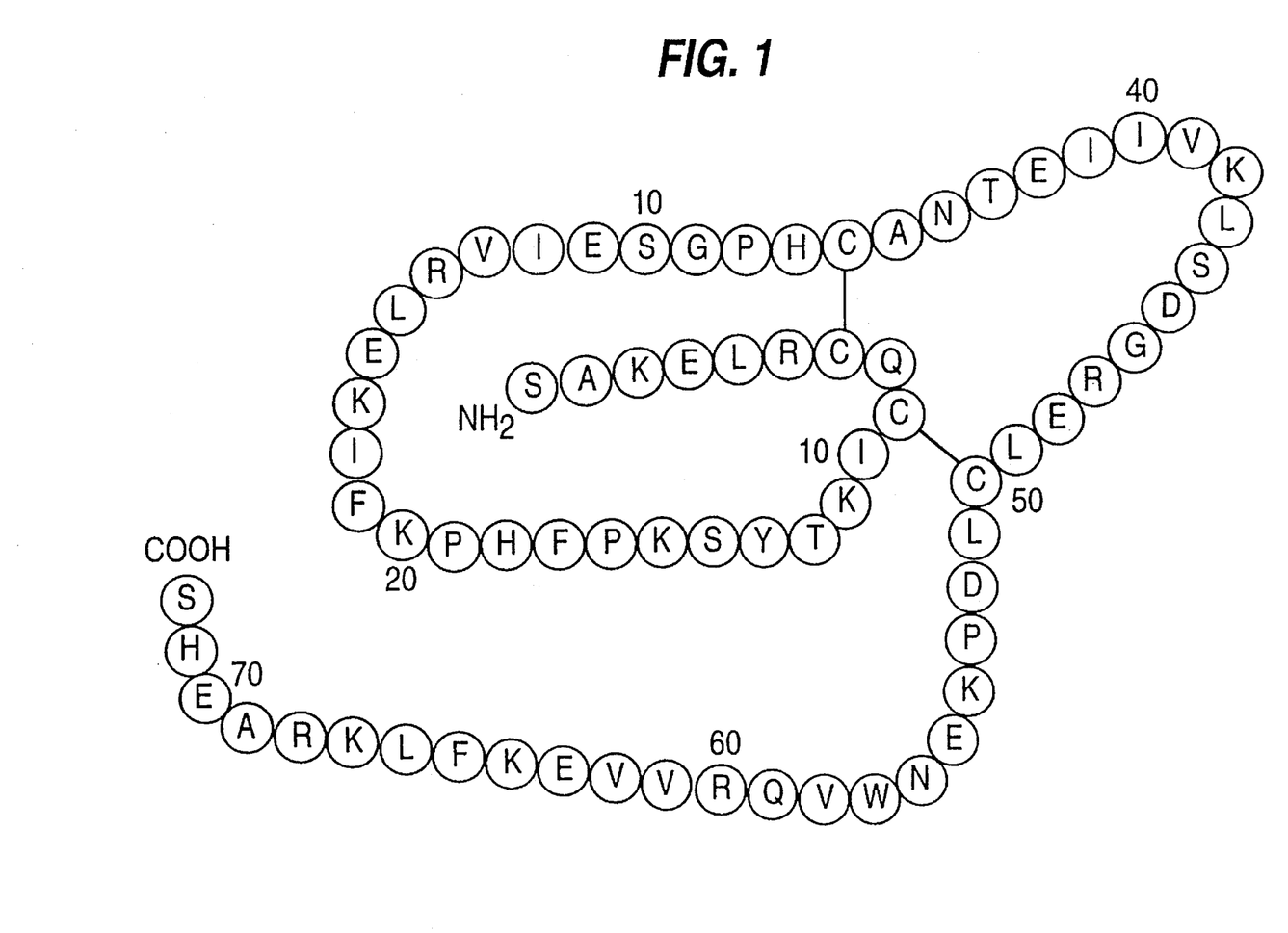
FIG. 1 is a schematic representation of an Interleukin-8 molecule (SEQ ID No: 2) capable of being utilized in accordance with one aspect of the present invention.

The amino acid sequence of Interleukin-8 is shown in FIG. 1, wherein the circled letters represent amino acids as follows: A represents Alanine, R represents Arginine, N represents Asparagine, D represents Aspartic acid, C represents Cysteine, Q represents Glutamine, E represents Glutamic acid, G represents Glycine, H represents Histidine, I represents Isoleucine, L represents Leucine, K represents Lysine, F represents Phenylalanine, P represents Proline, S represents Serine, T represents Threonine, W represents Tryptophan, Y represents Tyrosine and V represents Valine, or a suitable derivative thereof.

The members of the CXC chemokine family are generally characterized by having an ELR amino acid sequence immediately proceeding a conserved CXC sequence with four cysteine residues, the first two being separated by a variable amino acid (X) therebetween.

An ELR sequence can be added to a chemokine material which does not possess an ELR amino acid sequence, such as the CXC chemokine Platelet Factor 4, thereby facilitating binding to IL-8 receptors. The invention is thus applicable to labelled peptides which include one or more ELR or ELRC sequences therein.

The present invention is further applicable to derivatives of CXC chemokines, having specificity for receptors of CXC chemokines, in which retroinverse or other non-hydrolyzable linkages have been inserted, or D-amino acids substitutions have been made or peptidomimetic organic molecules have been utilized, in order to modify the native L-amino acid-containing sequence.

As noted above, the CXC chemokine carries a label or radioactive agent such as indium, iodine, technetium, rhenium, gallium, samarium, holmium, yttrium, copper, cobalt and the like. In particularly preferred embodiments, the CXC chemokine material carries a radioactive label selected from the group consisting of technetium-99m, indium-111, copper-62 and iodine-123.

The chemokine material can employ any suitable means for carrying the label or radioactive agent. Known methods for labelling peptides include the conventional "post-formed chelate approach" and the more recent "preformed chelate approach" developed by Fritzburg et al., U.S. Pat. Nos. 4,965,392 and 5,037,630, incorporated herein by reference. In the "pre-formed approach," the chelating agent is complexed with a radionuclide and then conjugated to the peptide. In the "post-formed approach," the chelating agent is first conjugated to the peptide and the resulting conjugate is incubated with radionuclide along with a reducing agent.

Suitable chelating agents for use in the present invention include triamide thiolate ($N_3S$) chelating agents such as represented by formula (I) and (Ia) below, diamide dithiolate ($N_2S_2$) chelating agents such as represented by formula (II) below and diamide diphenolic chelating agents such as represented by formula (III) below:

(I)

Wherein m in formulas (I), (Ia), (II) and (III) is a whole number of from 1 to about 10 (in formulas (I), (Ia) and (II), m preferably is about 3); P in formula (I) is either 0 or 1; Y of formula (Ia) is o- or p- nitrophenyl, 2-chloro-4-nitrophenyl, cyanomethyl, 2-mercaptopyridyl, hydroxybenztriazole, N-hydroxysuccinimide, trichlorophenyl, tetrafluorophenyl, thiophenyl, tetrafluorothiophenyl, tetrafluorophenyl, thiophenyl, tetrafluorothiophenyl, o-nitro-p-sulfophenyl or N-hydroxyphthalimide, most preferably tetrafluorophenyl; PG in formulas (I) and (II) is a suitable sulfur protecting group (each of which may be the same or different in formula II) selected from the group consisting of S-acyl groups of from 1 to about 20 carbon atoms such as alkanoyl, benzoyl and substituted benzoyl (wherein alkanoyl is preferred), S-alkyl groups of from 1 to about 20 carbon atoms such as benzyl, t-butyl, trityl, 4-methoxybenzyl and 2,4-dimethoxybenzyl (wherein 2,4-dimethoxybenzyl is preferred), alkoxyalkyl groups of from 1 to about 10 carbon atoms such as methoxymethyl, ethoxyethyl and tetrahydropyranyl (wherein tetrahydropyranyl is preferred), carbamoyl, and alkoxy carbonyl groups of from 1 to about 10 carbon atoms such as t-butoxycarbonyl, methoxycarbonyl and ethoxycarbonyl (wherein t-butoxycarbonyl is preferred); X is a coupling moiety selected from the group consisting of carboxyl, amino, isocyanate, isothiocyanate, imidate, maleimide, chlorocarbonyl, chlorosulfonyl, succinimidyloxycarbonyl, haloacetyl, and N-alkoxycarbamoyl groups of from 1 to about 10 carbon atoms such as N-methyoxycarbamoyl and t-butoxycarbamoyl (wherein in formulas (I) and (II), N-methoxycarbamoyl is preferred); and R of formula (III) is selected from the group consisting of hydrogen and alkyl groups of from 1 to about 10 carbon atoms such as methyl and t-butyl (wherein t-butyl is preferred).

Suitable sulfur-protecting groups, when taken together with the sulfur atom to be protected, include hemithioacetal groups such as ethoxyethyl, tetrahydrofuranyl, methoxymethyl, and tetrahydropyranyl. Other suitable sulfur protecting groups are acyl groups of from 1 to about 20 carbon atoms, preferably alkanoyl or benzoyl. Other possible chelating compounds are described in the European Patent Application assigned publication number 0 284 071 incorporated herein by reference.

Synthesis of a radiolabelled chelating agent, such as a Tc-99m bifunctional chelate, and subsequent conjugation to the chemokine material, can be performed as described in European Patent Application publication number 0 284 071 (supra), U.S. Pat. No. 4,965,392 (supra), and related technologies as covered by U.S. Pat. Nos. 4,837,003, 4,732,974 and 4,659,839, each incorporated herein by reference.

In accordance with one embodiment, the present invention comprises a chemokine,material conjugated with an unlabelled chelating agent, which later can be used to chelate with a suitable label or radioactive agent.

Chemokine material can also be labelled with halogen isotopes such as iodine-123 and iodine-131 using oxidation reactions.

In preferred embodiments utilizing a halogen label, chemokine material is labelled with a radioactive halogen such as iodine-123 or iodine-131 utilizing chloramine-T hydrate.

In accordance with the present invention, the chemokine material can be utilized to carry a label or radioactive agent to a target site of an animal, such as a human or other mammal.

A lysine of a chemokine material such as a CXC chemokine can be utilized to carry indium-111. A tyrosine, iodophenyl derivative or lysine (using Bolton-Hunter reagent) of the chemokine can be utilized to carry iodine-123. A lysine, alpha amine or added free cysteine of the chemokine can be utilized to carry technetium-99m. In still another embodiment, a chemokine material such as a CXC chemokine is labelled with a radioactive agent such as indium-111 utilizing a chelating agent such as diethylenetriaminepentaacetic acid.

According to one embodiment, radiolabelled CXC chemokine is injected into an animal's body and allowed to accumulate at a target site of inflammation and/or infection. Interleukin-8 has been found to be a very potent attractant for neutrophils produced by T-lymphocytes, monocytes, vascular endothelium and other tissues. Accordingly, radiolabelled Interleukin-8 is particularly suitable for imagining sites of inflammation and infectious disease in the body. Such sites include Interleukin-8 receptor molecules having areas which are complementary to corresponding Interleukin-8 material.

According to another embodiment, radiolabeled CC material is injected into an animal's body and allowed to accumulate at a target site of infection, inflammation, neoplasm atheromatous lesion or restenosis. As noted above, MCP-1 has a high degree of specificity for monocytes and macrophage cells, and is a potent stimulator of monocyte chemotaxis. Accordingly, radiolabelled MCP-1 is particularly suitable for imaging sites of infection, inflammation, neoplasm, atheromatous lesion or restenosis in the body.

The radiolabelled chemokine material is injected into the subject in a pharmaceutically acceptable carrier, such as an aqueous medium.

Pharmaceutically acceptable carriers include those that are suitable for injection or administration such as aqueous buffer solutions, e.g. tris (hydroxymethyl) aminomethane (and its salts), phosphate, citrate, bicarbonate, and the like, sterile water for injection, physiological saline, and balanced ionic solutions containing chloride and/or bicarbonate salts of normal blood plasma cations such as $Ca^{2+}$, $Na^+$, $K^+$, and $Mg^{2+}$. The carriers may contain a chelating agent, e.g. a small amount of ethylenediaminetetraacidic acid, calcium disodium salt, or other pharmaceutically acceptable chelating agents.

Generally, a diagnostically effective dosage of radiolabelled chemokine material will vary depending on considerations such as age, condition, sex, and extent of disease in the subject individual, counter indications, if any, and variables, to be adjusted by the individual physician. For example, dosage can vary from about 0.01 µg/kg to about 2000 µg/kg, and in more preferred embodiments from about 0.1 µg/kg to about 1000 µg/kg.

The radiolabelled chemokine material can begin to accumulate within approximately 15 minutes after injection into the subject, and in vivo imaging can be performed utilizing conventional imaging equipment for up to 24 hours or more after injection. Known imaging methods include conventional gamma camera techniques, single photon emission computerized tomography (SPECT), and other radionuclide scans.

After accumulating at the target site, the labelled chemokine material is gradually cleared from the target site and the animal's system by normal bodily function.

The invention is further illustrated by the following examples, which are not intended to be limiting.

EXAMPLE 1

Radiolabeling of Interleukin-8 with Technetium-99m.

A solution of CXC chemokine such as IL-8 (1.0 µmol), in 0.5 mL of carbonate/bicarbonate buffer at pH 8.5±0.5 is treated with a solution of 10.0 µmol of the ligand of formula I above (wherein m=2, p=1, PG is benzoyl, and X is succinimidyloxycarbonyl) in dimethylformamide (0.1 mL) and the entire mixture is kept at room temperature for 2 hours. The mixture is then diluted with water (2.5 mL) and dialyzed extensively against water or 0.1M ammonium bicarbonate, pH 7.5. After dialysis, the solution is lyophilized to give the desired IL-8 conjugate.

EXAMPLE 2

A solution of CXC chemokine such as IL-8 (1.0 µmol), in 0.5 mL of carbonate/bicarbonate buffer at pH 8.5±0.5 is treated with a solution of 10.0 µmol of the ligand of formula (II) above (wherein m=2, both PG are benzoyl, and X is succinimidyloxycarbonyl) in dimethylformamide (0.1 mL) and the entire mixture is kept at room temperature for 2 hours. The mixture is then diluted with water (2.5 mL) and dialyzed extensively against water or 0.1M ammonium bicarbonate, pH 7.5. After dialysis, the solution is lyophilized to give the desired IL-8 conjugate.

EXAMPLE 3

A solution of CXC chemokine such as IL-8 (1.0 µmol) in 0.5 mL of carbonate/bicarbonate buffer at pH 8.5±0.5 is treated with a solution of 10.0 µmol of the ligand of formula (III) above (wherein m=4, X is succinimidyloxycarbonyl and R is hydrogen) in dimethylformamide (0.1 mL) and the entire mixture is kept at room temperature for 2 hours. The mixture is then diluted with water (2.5 mL) and dialyzed extensively against water or 0.1M ammonium bicarbonate, pH 7.5. After dialysis, the solution is lyophilized to give the desired IL-8 conjugate.

EXAMPLE 4

To 100 uL of a solution containing 5 mg of sodium gluconate and 0.1 mg of stannous chloride in water, 500 ul of 99m-TcO4 (pertechnetate) is added. After incubation for about 10 minutes at room temperature, a solution of 500 uL of the IL-8 conjugate (1 mg/mL in 0.1M carbonate/bicarbonate buffer, pH 9.5) of Example 1, 2 or 3 is then added and the entire mixture is incubated at 37° C. for about 1 hour. The desired labelled peptide is separated from unreacted 99 mTc-gluconate and other small molecular weight impurities by gel filtration chromatography (Sephadex G-50) using phosphate buffered physiological saline, (hereinafter PBS), 0.15M NaCl, pH 7.4 as eluent.

EXAMPLE 5

Radioiodination of Interleukin-8, Chloramine-T Hydrate Method.

The following reagents and materials are prepared for radioiodination of Interleukin-8:

A) Chloramine-T Hydrate (freshly prepared) (FW=227.7) (Store stock desiccated, in vacuo, in dark, ambient temperature)
  1. Weigh out 10.0 mg and dilute with 5.0 ml of 0.05M Phosphate Buffer, pH 6.8.
  2. Take 1.0 ml of dilution and add 9.0 ml 0.05M Phosphate Buffer, pH 6.8 in volumetric flask.
  3. Concentration=0.2 mg/ml; use 45 µl /exp.=39.5 nmoles.

B) 0.05M Sodium Phosphate Buffer, Dibasic, pH 6.8. (FW=268.07) (For Chloramine-T, Metabisulfite, dilution and Reaction).
  1. Weigh out 1.3404 gm and dilute to 80 ml ($H_2O$).
  2. Adjust pH to 6.8, bring to total volume of 100 ml in volumetric flask.

C) 0.25M Sodium Phosphate Buffer, Dibasic, pH 6.8. (FW=268.07) (Reagent for buffering NaI-123 during reaction).
  1. Weigh out 6.7018 gm and dilute to 80 ml ($H_2O$) .
  2. Adjust pH to 6.8, bring to total volume of 100 ml in volumetric flask.

D) Sodium Metabisulfite (Freshly Prepared) (FW=190.1).
  1. Weigh out 20.0 mg and dilute with 5.0 m of 0.05M Sodium Phosphate Buffer.
  2. Take 1.0 ml of this solution and add 9.0 ml 0.05M Sodium Phosphate Buffer.
  3. Concentration=0.4 mg/ml; use 45 µl=18.0 µg/exp.= 94.5 nmoles.

E) Phosphate Buffered Saline
  1. Dissolve Sigma (PBS) prepared powder in 1.0 liter of millipore $H_2O$. Sigma cat. #1000-3.
  2. Check pH, should be 7.4.

F) BioRad AG1-X8 Anion Resin 100–200 mesh, Acetate form.
  1. Prepare slurry by suspending 6.4 gms of resin in 10 ml PBS.

G) Potassium Iodide Solution (For testing Chloramine-T solution before use in reaction)
  1. Weight out 0.25 gm KI and dilute with 5.0 ml ($H_2O$).
  2. Add several drops of the Chloramine-T solution to the KI solution.

3. A color change from a clear to light yellow solution should be observed, if the Chloramine-T solution is reactive.

H) Microfuge Tubes
  1. Sigma siliconized, 1.7 ml, polypropylene, Cat. # T-3406.

I) Sodium Iodine-123
  1. Mallinckrodt Medical, Inc.

J) Interleukin-8 (assuming FW=8,000)
  1. Use 10 μg per radioiodination=1.25 nmoles. Pepro Tech Inc.

The following preparations are undertaken prior to running the reaction:

A slurry is prepared of 90% v/v BioRad AG1-X8, 100–200 mesh, acetate form, 24 hours prior to use, with Phosphate Buffered Saline. 2.0 ml of the slurry is poured into a small AG1-X8 column, which then is washed with 10.0 ml Phosphate Buffered Saline. 45.0 μl Chloramine-T (freshly prepared), is pre-drawn into a Hamilton syringe after testing it with 5.0% KI. 45.0 μl Metabisulfite (freshly prepared) is pre-drawn into a Hamilton syringe. 50.0 μl Phosphate Buffered Saline is pre-drawn into a tuberculin syringe, and the syringe is labelled "R". 10.0 ml of Phosphate Buffered Saline is poured into a beaker, and set beside the column, for elution of the column.

Interleukin-8 is labelled with iodine-123 as follows:

To a siliconized microfuge tube reaction vial (1.7 ml), add (12.5 μg) IL-8 in 0.125 ml 0.05M Phosphate Buffer, pH 6.8. Add (50.0 μl) 0.25M Phosphate Buffer, pH 6.8 to the reaction vial and gently swirl. Add (20 μl) 20 nanograms "cold" iodide and gently swirl. Add (10–20 μl), 2.0 mCi, NaI-123 to the reaction vial and gently swirl. Add (45.0 μl) of Chloramine-T to the reaction vial, with a pre-drawn Hamilton syringe, and gently swirl. Incubate for 1.5 minutes at room temperature.

Add (45.0 μl) of Metabisulfite to the reaction vial, with a pre-drawn Hamilton syringe, and gently swirl. Assay reaction vial on a Capintec dose calibrator.

After reaction mixture has been assayed, place entire volume on prepared AG1-X8 column. Add (50 μl) PBS to reaction vial and swirl, then add to reaction mixture on column. Unplug column and collect 8 drops in the first tube. Then collect 2 drops in the next 24 tubes. The Vo will be in approximately tube #6. Use 1.7 ml siliconized microfuge tubes. Assay collected fractions on the Capintec dose calibrator. Combine the major fractions starting at the void volume. (NOTE: An aliquot should be taken for a dose assay for accurate results, if tissue distribution studies are being done.) Run TLC of sample in order to observe any free I-123. Spot a very small aliquot on a Gelman ITLC-SG strip, and develop with N-saline for 8 to 10 minutes. Cut into 1.0 cm sections and count on auto-gamma counter. Unreacted I-123 migrates at or near solvent front, protein remains at origin, small peptides have varying Rf values, at or near the origin.

EXAMPLE 6

Indium-111 Radiolabelling of Interleukin-8

The following reagents and materials are prepared prior to running the reaction:

A) Cyclic-Diethylenetriaminepentaacetic acid dianhydride (C-DTPA), FW—357.22 is synthesized and kept in a desiccator, in vacuo, at room temperature.

B) Commercially available Dimethylsulfoxide anhydrous (DMSO) is further purified by fractional freezing at or below 18.4° C. 20 to 25 ml of DMSO is placed in an oven dried 100 ml bottle and tightly capped. The bottle is placed in a slurry ice water bath and swirled until liquid solidifies on the walls of the bottle. An oven dried Pasteur pipet is used to remove remaining liquid. The bottle is capped and stored at room temperature under nitrogen, in a desiccator. Aldrich, 27, 685-5.

C) Nitrogen Gass is grade #5. Airco

D) Phosphate Buffered Saline (PBS)
  1. Dissolve Sigma (PBS) prepared powder in 1.0 liter of millipore water.
  2. Check pH, should be 7.4 Sigma, 1000-3

E) Phosphate Buffered Saline+5.0% BSA (For equilibration of G-25 column)
  1. To 10.0 ml PBS dissolve 0.5 g BSA.
  2. Final concentration 50.0 mg/ml BSA.

F) Phosphate Buffered Saline+0.5% BSA (For elution of G-25 column)
  1. To 50.0 ml PBS dissolve 0125 g BSA.
  2. Final concentration 5.0 mg/ml BSA.

G) G-25, medium grade
  1. Weigh out desired amount and swell in PBS for 24 hours.
  2. Before use degas for 24 or more hours.
  3. 24 hours prior to radiolabelling pour columns and equilibrate and wash with BSA/PBS solutions.
  4. Size of columns to be determined experimentally.

H) 0.10M diethylenetriaminepentaccetic acid (DTPA), FW=393.20
  1. Weigh out 0.393 gm DTPA and place in 8.0 ml PBS.
  2. Adjust pH to 5.4, bring to total volume of 10.0 ml in a volumetric flask. (Needs to become acidic for solubility) Sigma, D-6518

I) Millipore water

J) 111-Indium chloride (111-InCl3) in 0.05 N HCl Nordion International, Kanata, Canada, T209A (NOTE: In order to avoid hydrolysis and trace metal contamination, all reagents should be of the highest purity, DMSO should be purified by fractional freezing, all glassware and instruments should be thoroughly cleaned and rinsed approximately three times with millipore filtered water, and glassware and instruments to be used in the chelation reaction should be oven dried for approximately 24 hours at about 140° C. and cooled in a desiccator.)

The reaction is run as follows:

In step 1, C-DTPA (11.075 mg) is dissolved in 5.0 ml anhydrous DMSO. The tube is covered with parafilm, and gently inverted until the solution becomes clear. To 10 μg lyophilized IL-8 is added 0.5 ml PBS, pH 7.4. Add 0.01 ml (22.32 μg) C-DTPA/DMSO from step #1. Incubate solution, at room temperature, for 50 minutes. Gently swirl solution every 15 minutes. After incubation, place entire volume on the prepared G-25 column. Collect 0.20 ml fractions. Combine fractions at Vo and several fractions after the void volume. For Vo determination, use blue dextran. 111-InCl3 is assayed on a Capintec dose calibrator and 1.0 to 2.0 mCi of 111-In is pipetted into the IL-8 tube. The tube is gently swirled and assayed for the amount of radioactivity. The 111-In/IL-8 solution is incubated for 30 minutes, at room temperature. Excess 111-In is chelated to prevent the formation of indium hydroxide, an insoluble precipitate. The reaction mixture is loaded on a G-25 column and eluted with either PBS or 0.50% BSA, PBS. 0.20 ml fractions are collected. Fractions are assayed either on the dose calibrator or dilute aliquots of the fractions for counting on the gamma counter. Combine the fractions at the Vo (protein peak) and fractions after the void volume until the radioactivity levels decline. The excess chelated 111-In is eluted at or near the Vt. The combined Vo fractions are assayed on the dose calibrator and the radiolabelling efficiency are calculated. The empty reaction tube is also assayed to assure transfer of the majority of radioactivity.

EXAMPLE 7

Imaging with Radiolabelled Interleukin-8

White, male, Sprague-Dawley rats, weighing between 200–250 gm were used for imaging of inflammatory lesion. The lesion was induced by injecting 4.0 ml of 2.0% carrageenan (iota form), suspended in n-saline, into the hind limb. The other hind limb was used as a control and was injected with 4.0 ml saline. The hind limbs were selected, instead of IP or Sub-Q injections of carrageenan on the body of the rats, because less background activity is present for these studies.

The lesion was induced at various times prior to the injection of the radiolabelled IL-8. A difference in uptake of radioactivity was observed in the carrageenan limb, as compared to the control limb, when the radiolabelled IL-8 was injected 3 hours to 24 hours post lesion induction.

Routinely, images were acquired serially every 15 minutes for 3.0 hours post radiolabel injection. 15 minute images were also acquired every 24 hours post injection, until the labelled IL-8 was cleared from the animal.

Different cameras and collimators are used, depending on the radionuclide. With I-123 and Tc-99m, A Siemens, Z LC Orbiter camera and a 140 KeV, high resolution collimator were effective. With In-111 the same camera was used with a medium energy collimator. With I-125, a Siemens low energy mobile camera with a high sensitivity collimator was used. Image acquisition and storage, on all cameras, was accomplished by a Siemens MicroDelta computer, connected to a larger MicroVAX.

EXAMPLE 8

Comparison of I-125-Labeled Human Recombinant Interleukin-8 (I-125-IL-8) with Agents Ga-67 Citrate and In-111-Labeled Human Leukocytes for the Ability to Image a Sterile Acute Inflammatory Lesion in the Rat Hindlimb Recombinant human interleukin-8 was obtained from Pepro Tech Inc. I-125 was purchased as NaI from Amersham Corp. Ga-67 citrate and In-111-oxine were obtained from MediPhysics. Tc-99m (obtained from a Mo-99/Tc-99m generator) and TechneScan® PYP® were supplied by Mallinckrodt Medical, Inc. Carrageenan (iota from, Type V) was purchased from Sigma Chemical Co. (St. Louis, Mo.). All other reagents and supplies were of the highest grade commercially available.

IL-8 was radioiodinated following recommendations of the radionuclide supplier. Typically, 25–50 µg of IL-8 in 0.1 ml of 0.25M sodium phosphate, pH 6.8, was added one mass equivalent of non-radioactive NaI in a volume of 0.01 ml, followed by 2 mCi (0.02 ml) of I-125 as sodium iodide and 20 nmol (0.01 ml) of chloramine-T. Reactants were mixed and agitated gently for 90 sec at room temperature. The reaction was quenched by addition of 42 nmol (0.02 ml) of sodium metabisulfite. I-125-IL-8 was separated from non-reacted I-125 by ion exchange on a small column of Bio-Rad AG 1-X8, 50–100 mesh. The recovered product was stored at 4° C. until used, and injected within 6 hours after labeling.

Human leukocytes were prepared from a healthy donor and labeled with In-111-oxine, and rate erythrocytes were labeled in vivo (injecting TechneScan® PYP® and sodium Tc-99m pertechnetate into the tail vein of each rat) following recommendations of the radionuclide suppliers.

Radiolabeling efficiency was determined in a Beckman Gamma 8000 counter, and the proportion of protein-bound I-125 in the final product was routinely assessed by chromatography on ITLC-SG strips (Gelman) developed in 80% aqueous methanol. SDS-polyacrylamide gel electrophoresis and autoradiography were performed. Chemotaxis of human neutrophils toward nonlabeled IL-8 and I-125-IL-8 was evaluated in a Boyden chamber assay. Specific and nonspecific binding of I-125-IL-8 to isolated human neutrophils were determined.

Male Sprague-Dawley rats (Charles River), 200–250 grams, were housed in small groups under conditions approved by the institutional animal care committee, in compliance with guidelines of the American Association of Laboratory Animal Science. Animals were given ad libitum access to standard rat chow (Purina) and drinking water. Prior to lesion induction, injection of radiopharmaceutical, and imaging, each rat was given up to 13 mg/kg xylazine and 87 mg/kg ketamine subcutaneously in the interscapular region. Additional small doses of ketamine were given as necessary to maintain an adequate level of sedation during the image acquisition.

Acute inflammatory lesions were induced by subcutaneous injection of 4 ml of carrageenan suspension (2% w/v in sterile saline) into the left thigh of each rat. The right (control) thigh was injected with 4 ml of sterile saline. Twenty-four hours later each rat received a single radiopharmaceutical agent, 50–100 µCi in ≦0.5 ml, by aseptic injection under direct visualization into the right external jugular vein. For the results reported here each inflammation-imaging radiopharmaceutical was injected into four rats, and three rats' erythrocytes were radiolabeled in vivo.

Posterior total body gamma camera images were acquired beginning 15 min following radiopharmaceutical injection and at selected intervals up to 96 hours postinjection. Sedated rats were placed in pairs in their backs atop an inverted camera head with a protective layer over the collimator, and taped to the layer to maintain optimum limb position. Calibration standards corresponding to known fractions of the injected activity for each agent were diluted in scintillation vials to approximate the thickness of the rat thigh, and place upon the covered collimator for concurrent imaging. Images of I-125 and Tc-99m activity in this series of experiments were acquired on a Siemens LEM Plus mobile camera with a low energy, high sensitivity collimator, and images of In111 and Ga-67 activity on a Siemens Orbiter camera using a medium energy collimator. Most acquisitions were obtained over a period of fifteen minutes.

Relative activity was determined by computer-assisted region-of-interest analysis for each hindlimb, for each calibration standard, and for appropriate background regions at each imaging session. Regional counts were converted to percent injected activity corrected for background and for physical decay, and expressed as a function of time postinjecton. Graphical and statistical analysis of the converted data utilized the programs Excel (Microsoft), Minitab (Minitab, Inc.), and Sigmaplot (Jandel Scientific).

The physical and biological integrity of IL-8 were well preserved during the radiolabeling procedure. Assuming complete physical recovery of IL-8 from the labeling mixture, specific activities of 88–138 Ci/mmol were achieved, representing radiolabelling efficiencies of 14–45%. Protein-bound radioactivity accounted for 95–98% of the total activity in the final product. The electrophoretic mobility of I-125-IL-8 on SDS-polyacrylamide gels was indistinguishable from that of nonlabled IL-8, and I-125-IL-8 was ≧95% as effective as nonlabeled IL-8 with respect to neutrophil chemotaxis when assayed in a Boyden chamber. To asses its receptor-binding properties, we incubated I-125-IL-8 with purified human neutrophils over a 30-fold range of concentrations, both alone (in triplicate) and in the presence of a 1000-fold molar excess of nonlabeled IL-8 (in duplicate) at each concentration. Specific binding of I-125-IL-8, expressed as the difference between activity bound in the absence and in the presence of competitor, accounted for ≧90% of the total binding observed. In agreement with the findings of other investigators, analysis of the binding curves indicated an abundance of high-affinity receptors (estimated maximum of ~60,000 binding sites per cell; $k_d$=8.3E-10M).

Posterior images of individual rats were obtained 1 to 24 hours following intravenous injection of I-125-IL8,Ga-67 citrate, and In-111-labeled human leukocytes. These three agents yielded qualitatively similar images, exhibiting asymmetrically increased activity in the left hindlimb compared to the right at all times postinjection.

Persistent asymmetry until at least 96 hours postinjection for all three agents was confirmed. However, the time course of hindlimb activity differed according to the agent given. Left hindlimb I-125-IL-8 activity peaked between one and three hours postinjection, with a calculated means value and standard deviational three hours of 4.8±0.5% of the injected activity corrected for physical decay (%IA), and declined in roughly exponential fashion thereafter. In-111-WBC activity in the left hindlimb also increased rapidly, reaching a value of 4.2±0.6%IA by three hours postinjection and an eventual plateau (4.5±0.4%IA at 24 hours). Left hindlimb Ga-67 activity rose briefly to 9.2±0.5%IA by six hours postinjection, and subsequently declined to a constant level of about 7.5%IA.

For rats injected with I-125-IL-8 or In-111-WBC, left hindlimb activity was significantly greater than right hindlimb activity at all imagining time points (p≦0.05). For the rats injected with Ga-67 citrate, differences between left and right hindlimb activity were significant at all time points except 1 hour postinjection (p+0.2).

Rats given I-125-IL-8 demonstrated the most marked asymmetry of hindlimb activity partitioning, with a mean left:right hindlimb activity ratio (L/C) of 2.5±0.9 for all imaging time points, and with no significant temporal variation. By analysis of variance, this ratio was significantly higher (p<0.001) than the corresponding ratio (1.5±0.3) in rats given either Ga-67 citrate or IN-111-WBC.

In order to determine whether differential limb perfusion in response to the inflammatory focus could account for such asymmetry, an additional three carrageenan-treated rats were injected intravenously with stannous pyrophosphate and Tc-99m pertechetate to label their erythrocytes in vivo. Because of the short physical half-life and in vivo degradation of the radiotracer, comparison between this blood pool agent and the inflammation-imaging agents was limited to analysis of images obtained ≦24 hours postinjection. As expected, activity in the left hindlimb was highest immediately after erythrocyte labeling (mean 3.1 ±1.0 %IA) and decline to 1.6±0.5%IA by 24 hours. The mean L/C ratio and standard deviation calculated between 0 and 24 hours postinjection for rats carrying Tc-99m-labeled erythrocytes was 1.2±0.2. This ratio is significantly lower than that for rats injected with I-125-IL-8, but surprisingly, it is not significantly different from the L/C ratios of rats receiving Ga-67 citrate of In-111-WBC.

The above demonstrates that I-125-labeled human recombinant interleukin-8 (I-125-IL-8) compares favorably with both Ga-67 citrate and In-111-labeled human leukocytes for imaging of carrageenan-induced acute inflammatory lesions in the rat hindlimb. In this Example, the postinjection time to peak activity for I-125-IL-8 is short, and the target-to-nontarget activity ratio for I-125-IL-8 is significantly higher than that for either agent of comparision or for a radiotracer of blood pool activity.

Without being bound to any particular theory about how I-125-IL-8 selectively appears in the inflammatory focus, the observations suggest that the interactions between IL-8 and neutrophils that have been established through in vitro experimentation may account for the in vivo behavior of I-125-IL-8. Rapid influx of IL-8 into a neutrophil-rich region is entirely consistent with the functioning of a high abundance, high-affinity receptor-mediated process, and the subsequent exponential decline in lesion-associated activity appears logical following rapid internalization and degradation of the IL-8 ligand.

Initially, there was consideration of radiolabeling homologous rat leukocytes for comparison in this Example, but our attempts to prepare In-111-labeled leukocytes from normal rat blood resulted in unsatisfactory cell yield and labeling efficiency. Wishing neither to confound our experimental model by infusing exogenously stimulated leukocytes nor to exsanguinate rats needlessly, we elected to use readily available normal human leukocytes.

IL-8 offers several a priori advantages for clinical nuclear imagining. As a naturally occurring human polypeptide commercially available in recombinant (and potentially synthetic form), it is both contagion-free and nonimmunogenic, without known toxic effects in humans (unlike bacterial peptides). IL-8 is readily radioiodinated without detectably altering its physical or biological properties, and our work shows that IL-8 may also be radiolabeled with I-123 or In-111 to yield qualitatively comparable images in carrageenan-treated rats to those presented here. Radiolabeling and administration of IL-8 involve no handling of blood or time-consuming isolation of blood components, considerations that would make IL-8 an agent of choice in individuals harboring blood-borne transmissible infections, and in subjects for whom an urgent study is indicated. The size and solubility of IL-8 permit ready access to tissue neutrophils, with a minimal lag period expected between injection and satisfactory imageability. Finally, the affinity and high receptor number on neutrophils for IL-8 should result in considerable signal amplification in an acute inflammatory focus of infectious or noninfectious etiology. This feature would make radiolabeled IL-8 particularly useful for detecting focal accumulation of neutrophils in neutropenic subjects and small children, from whom comparatively large blood volumes must be drawn to isolate peripheral leukocytes for a direct radiolabeling procedure.

EXAMPLE 9

Imaging with I-125 Labelled IL-8 and I-125 Labelled NAP-2

Radiolabeled recombinant human Interleukin-8 (IL-8) was compared with human Neutrophil-activating Peptide 2

(NAP-2), a chemotactic cytokine with high sequence homology to IL-8 but exhibiting lower biological potency, for imagining acute sterile inflammatory lesions in rats. I-125-IL-8 and I-125-NAP-2 were prepared substantially as set forth in Example 5 above, by reaction with chloramine-T and repurified by ion exchange chromatography. Lesions were induced in eight male rats substantially as set forth in Example 7 above, by subcutaneous injection of 4 ml 2% carrageenan suspension into their left hindlimbs, with an equivalent volume of sterile saline injected into their right hindlimbs to serve as control sites. Twenty-four hours (24 h) later each rat received 0.05–0.1 mCi (1.8–3.7 MBq) of either agent intravenously. Total body gamma camera images were obtained 1 h, 3 h, 6 h, 24 h, 48 h, 72 h, and 96 h postinjection. Left hindlimb and right hindlimb activities were determined as regional percent injected activity corrected for physical decay (%IA). Time-activity curves for I-125-IL-8 and I-125-NAP-2 in the carrageenan-containing left hindlimbs were nearly identical: both peaked at 1–3 h postinjection (IL-8:4.8±0.5%IA; NAP-2:4.8±1.8%IA) and decreased exponentially thereafter. However, while the lesioned-to-control limb ratio (L/C) for I-125-IL-8 varied little (2.5±0.9) over the imaging period, L/C for I-125-NAP-2 rose from 1.5±0.4 at 1 h to 5.3±0.7 by 72 h postinjection. Uptake of I-125 NAP-2 took place as early as 30 minutes and this persisted to 96 hours when the experiment was terminated. Both radiolabeled IL-8 and NAP-2 appear useful for imagining. Radiolabeled NAP-2 may provide better discrimination of inflammatory lesions from normal tissue at later times postinjection.

EXAMPLE 10

Radiolabeling of MCP Material with Technetium-99m

A solution of MCP material such as MCP-1 (1.0 μmol), in 0.5 mL of carbonate/bicarbonate buffer at pH 8.5±0.5 is treated with a solution of 10 μmol of the ligand of formula I above (wherein m=2, p=1, PG is benzoyl, and X is succinimidyloxycarbonyl) in dimethylformamide (0.1 mL) and the entire mixture is kept at room temperature for 2 hours. The mixture is then diluted with water (2.5 mL) and dialyzed extensively against water or 0.1M ammonium bicarbonate, pH 7.5. After dialysis, the solution is lyophilized to give the desired MCP conjugate.

EXAMPLE 11

A solution of MCP material such as MCP-1 (1.0 μmol), in 0.5 mL of carbonate/bicarbonate buffer at pH 8.5±0.5 is treated with a solution of 10 μmol of the ligand of formula (II) above (wherein m=2, both PG are benzoyl, and X is succinimidyloxycarbonyl) in dimethylformamide (0.1 mL) and the entire mixture is kept at room temperature for 2 hours. The mixture is then diluted with water (2.5 mL) and dialyzed extensively against water or 0.1M ammonium bicarbonate, pH 7.5. After dialysis, the solution is lyophilized to give the desired MCP conjugate.

EXAMPLE 12

A solution of MCP material such as MCP-1 (1.0 μmol) in 0.5 mL of carbonate/bicarbonate buffer at pH 8.5±0.5 is treated with a solution of 10 μmol of the ligand of formula (III) above (wherein m=4, X is succinimidyloxycarbonyl and R is hydrogen) in dimethylformamide (0.1 mL) and the entire mixture is kept at room temperature for 2 hours. The mixture is then diluted with water (2.5 mL) and dialyzed extensively against water or 0.1M ammonium bicarbonate, pH 7.5. After dialysis, the solution is lyophilized to give the desired MCP conjugate.

EXAMPLE 13

To 100 uL of a solution containing 5 mg of sodium gluconate and 0.1 mg of stannous chloride in water, 500 ul of 99m-TcO4 (pertechnetate) is added. After incubation for about 10 minutes at room temperature, a solution of 500 uL of the MCP conjugate (1 mg/mL in 0.1M carbonate/bicarbonate buffer, pH 9.5) of Example 1, 2 or 3 is then added and the entire mixture is incubated at 37° C. for about 1 hour. The desired labelled peptide is separated from unreacted 99mTc-gluconate and other small molecular weight impurities by gel filtration chromatography (Sephadex G-50) using phosphate buffered physiological saline, (hereinafter PBS), 0.15M NaCl, pH 7.4 as eluent.

EXAMPLE 14

Radioiodination of MCP-1, Chloramine-T Hydrate Method.

The following reagents and materials are prepared for radioiodination of MCP-1:

A) Chloramine-T Hydrate (freshly prepared) (FW=227.7) (Store stock desiccated, in vacuo, in dark, ambient temperature)
  1. Weigh out 10.0 mg and dilute with 5.0 ml of 0.05M Phosphate Buffer, pH 6.8.
  2. Take 1.0 ml of dilution and add 9.0 ml 0.05M Phosphate Buffer, pH 6.8 in volumetric flask.
  3. Concentration=0.2 mg/ml; use 45 μl/exp.=39.5 nmoles.
B) 0.05M Sodium Phosphate Buffer, Dibasic, pH 6.8. (FW=268.07) (For Chloramine-T, Metabisulfite, dilution and Reaction).
  1. Weigh out 1.3404 gm and dilute to 80 ml ($H_2O$).
  2. Adjust pH to 6.8, bring to total volume of 100 ml in volumetric flask.
C) 0.25M Sodium Phosphate Buffer, Dibasic, pH 6.8. (FW=268.07) (Reagent for buffering NaI-123 during reaction).
  1. Weigh out 6.7018 gm and dilute to 80 ml ($H_2O$).
  2. Adjust pH to 6.8, bring to total volume of 100 ml in volumetric flask.
D) Sodium Metabisulfite (Freshly Prepared) (FW=190.1).
  1. Weigh out 20.0 mg and dilute with 5.0 ml of 0.05M Sodium Phosphate Buffer.
  2. Take 1.0 ml of this solution and add 9.0 ml 0.05M Sodium Phosphate Buffer.
  3. Concentration=0.4 mg/ml; use 45 μl=18.0 μg/exp.= 94.5 nmoles.
E) Phosphate Buffered Saline
  1. Dissolve Sigma (PBS) prepared powder in 1.0 liter of millipore $H_2O$. Sigma cat. #1000-3.
  2. Check pH, should be 7.4.
F) BioRad AG1-X8 Anion Resin 100–200 mesh, Acetate form.
  1. Prepare slurry by suspending 6.4 gms of resin in 10 ml PBS.
G) Potassium Iodide Solution (For testing Chloramine-T solution before use in reaction)
  1. Weight out 0.25 gm KI and dilute with 5.0 ml ($H_2O$).

2. Add several drops of the Chloramine-T solution to the KI solution.
3. A color change from a clear to light yellow solution should be observed, if the Chloramine-T solution is reactive.

H) Microfuge Tubes
 1. Sigma siliconized, 1.7 ml, polypropylene, Cat. # T-3406.

I) Sodium Iodine-123
 1. Mallinckrodt Medical, Inc.

J) MCP-1 (assuming FW=12,500)
 1. Use 10 µg per radioiodination=1.25 nmoles. Pepro Tech Inc.

The following preparations are undertaken prior to running the reaction:

A slurry is prepared of 90% v/v BioRad AG1-X8, 100–200 mesh, acetate form, 24 hours prior to use, with Phosphate Buffered Saline. 2.0 ml of the slurry is poured into a small AG1-X8 column, which then is washed with 10.0 ml Phosphate Buffered Saline. 45.0 µl Chloramine-T (freshly prepared), is pre-drawn into a Hamilton syringe after testing it with 5.0% KI. 45.0 µl Metabisulfite (freshly prepared) is pre-drawn into a Hamilton syringe. 50.0 µl Phosphate Buffered Saline is pre-drawn into a tuberculin syringe, and the syringe is labelled "R". 10.0 ml of Phosphate Buffered Saline is poured into a beaker, and set beside the column, for elution of the column.

MCP-1 is labelled with iodine-123 as follows:

To a siliconized microfuge tube reaction vial (1.7 ml), add (12.5 µg) MCP-1 in 0.125 ml 0.05M Phosphate Buffer, pH 6.8. Add (50.0 µl) 0.25M Phosphate Buffer, pH 6.8 to the reaction vial and gently swirl. Add (20 µl) 20 nanograms "cold" iodide and gently swirl. Add (10–20 µl), 2.0 mCi, NaI-123 to the reaction vial and gently swirl. Add (45.0 µl) of Chloramine-T to the reaction vial, with a pre-drawn Hamilton syringe, and gently swirl. Incubate for 1.5 minutes at room temperature.

Add (45.0 µl) of Metabisulfite to the reaction vial, with a pre-drawn Hamilton syringe, and gently swirl. Assay reaction vial on a Capintec dose calibrator.

After reaction mixture has been assayed, place entire volume on prepared AG1-X8 column. Add (50 µl) PBS to reaction vial and swirl, then add to reaction mixture on column. Unplug column and collect 8 drops in the first tube. Then collect 2 drops in the next 24 tubes. The Vo will be in approximately tube #6. Use 1.7 ml siliconized microfuge tubes. Assay collected fractions on the Capintec dose calibrator. Combine the major fractions starting at the void volume. (NOTE: An aliquot should be taken for a dose assay for accurate results, if tissue distribution studies are being done.) Run TLC of sample in order to observe any free I-123. Spot a very small aliquot on a Gelman ITLC-SG strip, and develop with N-saline for 8 to 10 minutes. Cut into 1.0 cm sections and count on auto-gamma counter. Unreacted I-123 migrates at or near solvent front, protein remains at origin, small peptides have varying Rf values, at or near the origin.

EXAMPLE 15

Indium-111 Radiolabelling of MCP-1.

The following reagents and materials are prepared prior to running the reaction:

A) Cyclic-Diethylenetriaminepentaacetic acid dianhydride (C-DTPA), FW—357.22 is synthesized and kept in a desiccator, in vacuo, at room temperature.

B) Commercially available Dimethylsulfoxide anhydrous (DMSO) is further purified by fractional freezing at or below 18.4° C. 20 to 25 ml of DMSO is placed in an oven dried 100 ml bottle and tightly capped. The bottle is placed in a slurry ice water bath and swirled until liquid solidifies on the walls of the bottle. An oven dried Pasteur pipet is used to remove remaining liquid. The bottle is capped and stored at room temperature under nitrogen, in a desiccator. Aldrich, 27, 685-5.

C) Nitrogen Gas is grade #5. Airco

D) Phosphate Buffered Saline (PBS)
 1. Dissolve Sigma (PBS) prepared powder in 1.0 liter of millipore water.
 2. Check pH, should be 7.4 Sigma, 1000-3

E) Phosphate Buffered Saline+5.0% BSA (For equilibration of G-25 column)
 1. To 10.0 ml PBS dissolve 0.5 g BSA.
 2. Final concentration 50.0 mg/ml BSA.

F) Phosphate Buffered Saline+0.5% BSA (For elution of G-25 column)
 1. To 50.0 ml PBS dissolve 0125 g BSA.
 2. Final concentration 5.0 mg/ml BSA.

G) G-25, medium grade
 1. Weigh out desired amount and swell in PBS for 24 hours.
 2. Before use degas for 24 or more hours.
 3. 24 hours prior to radiolabelling pour columns and equilibrate and wash with BSA/PBS solutions.
 4. Size of columns to be determined experimentally.

H) 0.10M diethylenetriaminepentaccetic acid (DTPA), FW=393.20
 1. Weigh out 0.393 gm DTPA and place in 8.0 ml PBS.
 2. Adjust pH to 5.4, bring to total volume of 10.0 ml in a volumetric flask. (Needs to become acidic for solubility) Sigma, D-6518

I) Millipore water

J) 111-Indium chloride (111-InC13) in 0.05 N HCl Nordion International, Kanata, Canada, T209A (NOTE: In order to avoid hydrolysis and trace metal contamination, all reagents should be of the highest purity, DMSO should be purified by fractional freezing, all glassware and instruments should be thoroughly cleaned and rinsed approximately three times with millipore filtered water, and glassware and instruments to be used in the chelation reaction should be oven dried for approximately 24 hours at about 140° C. and cooled in a desiccator.)

The reaction is run as follows:

In step 1, C-DTPA (11.075 mg) is dissolved in 5.0 ml anhydrous DMSO. The tube is covered with parafilm, and gently inverted until the solution becomes clear. To 10 µg lyophilized MCP-1 is added 0.5 ml PBS, pH 7.4. Add 0.01 ml (22.32 µg) C-DTPA/DMSO from step #1. Incubate solution, at room temperature, for 50 minutes. Gently swirl solution every 15 minutes. After incubation, place entire volume on the prepared G-25 column. Collect 0.20 ml fractions. Combine fractions at Vo and several fractions after the void volume. For Vo determination, use blue dextran. 111-InC13 is assayed on a Capintec dose calibrator and 1.0 to 2.0 mCi of 111-In is pipetted into the MCP-1 tube. The tube is gently swirled and assayed for the amount of radioactivity. The 111-In/MCP-1 solution is incubated for 30 minutes, at room temperature. Excess 111-In is chelated to prevent the formation of indium hydroxide, an insoluble precipitate. The reaction mixture on a G-25 column and eluted with either PBS or 0.50% BSA, PBS. 0.20 ml fractions are collected. Fractions are assayed either on the dose calibrator or dilute aliquots of the fractions for counting on the gamma counter. Combine the fractions at the Vo (protein peak) and fractions after the void volume until the radioactivity levels decline. The excess chelated 111-In is eluted at or near the Vt. The combined Vo fractions are assayed on the dose calibrator and the radiolabelling efficiency are calculated. The empty reaction tube is also assayed to assure transfer of the majority of radioactivity.

EXAMPLE 16

Imaging with radiolabelled MCP-1

White, male, Sprague-Dawley rats, weighing between 200–250 gm are used for imaging of inflammatory lesion. The lesion is induced by injecting 4.0 ml of 2.0% carrageenan (iota form), suspended in n-saline, into the hind limb. The other hind limb is used as a control and is injected with 4.0 ml saline. The hind limbs are selected, instead of IP or Sub-Q injections of carrageenan on the body of the rats, because less background activity is present for these studies.

The lesion is induced at various times prior to the injection of the radiolabelled MCP-1. A difference in uptake of radioactivity is observed in the carrageenan limb, as compared to the control limb, when the radiolabelled MCP-1 is injected 3 hours to 24 hours post lesion induction.

Routinely, images are acquired serially every 15 minutes for 3.0 hours post radiolabel injection. 15 minute images are also acquired every 24 hours post injection, until the labelled MCP-1 is cleared from the animal.

Different cameras and collimators are used, depending on the radionuclide. With I-123 and Tc-99m, A Siemens, Z LC Orbiter camera and a 140 KeV, high resolution collimator were effective. With In-111 the same camera was used with a medium energy collimator. With I-125, a Siemens low energy mobile camera with a high sensitivity collimator was used. Image acquisition and storage, on all cameras, was accomplished by a Siemens MicroDelta computer, connected to a larger MicroVAX.

EXAMPLE 17

Imaging with I-125 Labelled MCP-1

Two studies were completed with two groups of three rats utilizing I-125 as the radiolabel and MCP-1 as the CC chemokine. In both studies, I-125 labelling of MCP-1 was accomplished substantially in accordance with the procedure given in Example 14 above (Radioiodinization of MCP-1, chloramine-T hydrate method), with any substantial deviations therefrom noted below. The animals were injected with 4.0 ml of 2.0% carrageenan (Iota form) as indicated in Example 16 above (Imaging with radiolabelled MCP-1). In the first group, carrageenan was injected 3 days prior to injecting I-125 labelled MCP-1 ($^{125}$I-MCP-1). In the second group, the carrageenan was injected 24 hours prior to injecting $^{125}$I-MCP-1. The three-day group received 170 μCi per rat and the 24 hour group received 175 μCi per rat. A Siemens low energy mobile camera with a high sensitivity collimator was used for imaging.

These studies demonstrated that accumulation of I-125 labelled MCP-1 takes place as early as 30 minutes and persists to the termination of each respective experiment at either 48 hours or 72 hours. In no case did the control limb, injected with a comparable volume (4.0 ml) of physiological saline, indicate any significant accumulation at any time point.

Since many modifications, variations and changes in detail may be made to the described embodiments, it is intended that all matter in the foregoing description be interpreted as illustrative and not in a limiting sense.

---

We claim:

1. A method of imaging a target site in an animal body, comprising providing a radionuclide-labelled chemokine, wherein said chemokine is a Neutrophil-activating Peptide-2 (NAP-2) peptide, introducing the labelled chemokine into an animal's body, allowing said labelled chemokine to accumulate at a target site of the animal's body, wherein receptor molecules recognizable by said chemokine are located at said target site, and detecting the accumulated, labelled chemokine so as to image said target site.

2. The method of claim 1 wherein the NAP-2 peptide recognizes Interleukin-8 receptor molecules.

3. The method of claim 1 wherein said target site is an inflamed or diseased portion of said animal's body.

4. The method of claim 1 wherein said chemokine is labelled with indium-111, iodine-123, technetium-99m or copper-62.

5. The method of claim 4 wherein said chemokine is labelled with indium-111 utilizing a chelating agent.

6. The method of claim 5 wherein said chelating agent is C-DTPA.

7. The method of claim 4 wherein said chemokine is labelled with iodine-123 utilizing chloramine-T hydrate.

8. The method of claim 4 wherein said chemokine is labelled with technetium-99m.

9. The method of claim 1 wherein said chemokine is labelled utilizing a chelating agent.

10. The method of claim 9 wherein said chelating agent is a triamide thiolate ligand, a diamide dithiolate ligand or a diamide diphenolic ligand.

11. The method of claim 10 wherein said chemokine is labelled with technetium-99m or copper-62 and said chelating agent is a triamide thiolate ligand.

12. A method of delivering a labeling agent to a target site of an animal's body, comprising introducing into an animal's body a NAP-2 peptide carrying a radionuclide labeling agent, wherein receptor molecules recognizable by said NAP-2 peptide are located at said target site, and allowing the labeling agent-carrying NAP-2 peptide to accumulate at said target site, so as to deliver said labeling agent to said target site.

13. The method of claim 12 wherein said receptor molecules are Interleukin-8 receptor molecules.

14. A method of delivering a radioactive agent to a target site of an animal's body comprising introducing into an animal's body a NAP-2 peptide carrying a radioactive agent, wherein receptor molecules recognizable by said NAP-2 peptide are located at said target site, and allowing the radioactive agent-carrying NAP-2 peptide to accumulate at a target site, so as to deliver said radioactive agent to said target site.

15. The method of claim 14 wherein said receptor molecules are Interleukin-8 receptor molecules.

16. A composition comprising a chemokine material selected from the group consisting of CC chemokines and CXC chemokines, wherein C stands for cysteine and X stands for an amino acid other than cysteine, and wherein said chemokine material carries a radioactive agent selected from the group consisting of iodine-123 and iodine-131.

17. A NAP-2 peptide which recognizes Interleukin-8 receptor molecules, said NAP-2 peptide carrying a radioactive agent selected from the group consisting of technetium-99m, indium-111, copper-62, rhenium-186 and rhenium-188.

18. The composition of claim 16 wherein said chemokine is conjugated with said radioactive agent utilizing a chelating agent.

19. The composition of claim 16 wherein said chelating agent is a triamide thiolate ligand, diamide dithiolate ligand or diamide diphenolic ligand.

20. The composition of claim 16 wherein said chemokine material carries a radioactive agent selected from the group consisting of technetium-99m and copper-62.

21. The composition of claim 19 wherein said chemokine material carries a radioactive agent selected from the group consisting of technetium-99m and copper-62.

22. A method of imaging a target site in an animal body, comprising providing a radionuclide-labelled chemokine including an ELR amino acid sequence therein, wherein E stands for glutamic acid, L stands for leucine and R stands for arginine, introducing a detectable amount of said labelled chemokine into an animal's body, allowing said labelled chemokine to accumulate at a target site of the animal's body, wherein receptor molecules recognizable by said chemokine are located at said target site, and detecting the accumulated, labelled chemokine so as to image said target site.

23. The method of claim 22 wherein said receptor molecules are Interleukin-8 receptor molecules.

24. The method of claim 22 wherein said chemokine includes an ELRC sequence, wherein C stands for cysteine.

25. The method of claim 1 wherein said target site is a site of infection, inflammation, neoplasm, atheromatous lesion or restenosis of said animal's body.

* * * * *